United States Patent
Klefisch et al.

(10) Patent No.: US 11,103,225 B2
(45) Date of Patent: Aug. 31, 2021

(54) MEDICAL DEVICE, IN PARTICULAR FOR TREATING FISTULAS

(71) Applicant: B. BRAUN SURGICAL S.A., Rubi (ES)

(72) Inventors: Patricia Klefisch, Rubi (ES); Ivan Rosales Parral, Rubi (ES); Pau Turon Dols, Rubi (ES); Maria Eugenia Grandes Vilaclara, Rubi (ES); Ricardo Sanchez Garrido, Rubi (ES)

(73) Assignee: B. BRAUN SURGICAL S.A., Rubi (ES)

( * ) Notice: Subject to any disclaimer, the term of this patent is extended or adjusted under 35 U.S.C. 154(b) by 0 days.

(21) Appl. No.: 16/328,132

(22) PCT Filed: Aug. 15, 2017

(86) PCT No.: PCT/EP2017/070649
§ 371 (c)(1),
(2) Date: Feb. 25, 2019

(87) PCT Pub. No.: WO2018/041624
PCT Pub. Date: Mar. 8, 2018

(65) Prior Publication Data
US 2019/0183469 A1    Jun. 20, 2019

(30) Foreign Application Priority Data

Aug. 31, 2016  (EP) ..................................... 16186543

(51) Int. Cl.
*A61B 17/00* (2006.01)
*A61M 1/00* (2006.01)

(52) U.S. Cl.
CPC ........... *A61B 17/0057* (2013.01); *A61M 1/84* (2021.05); *A61M 1/90* (2021.05);
(Continued)

(58) Field of Classification Search
CPC ...... A61B 17/0057; A61B 2017/00641; A61B 17/221; A61B 17/12022; A61B 17/12113;
(Continued)

(56) References Cited

U.S. PATENT DOCUMENTS

| 8,900,268 B2 | 12/2014 | Weidenhagen et al. |
| 10,016,538 B2 | 7/2018 | Locke et al. |

(Continued)

FOREIGN PATENT DOCUMENTS

| CN | 2776446 | 5/2006 |
| CN | 101184468 A | 5/2008 |

(Continued)

OTHER PUBLICATIONS

Extended European Search Report for European Application No. 16 186 543.1, dated Feb. 15, 2017—8 pages.
(Continued)

*Primary Examiner* — Erich G Herbermann
*Assistant Examiner* — Chima U Igboko (57) ABSTRACT

A medical device includes a fluid collection element, a fluid communication element and a pulling element. The pulling element is attached to a distal end of the fluid collection element and/or fluid communication element. The medical device can be included in a medical kit.

16 Claims, 3 Drawing Sheets

(52) U.S. Cl.
CPC ............... *A61B 2017/00004* (2013.01); *A61B 2017/00641* (2013.01); *A61M 2210/1067* (2013.01)

(58) Field of Classification Search
CPC ........ A61B 17/12122; A61B 17/12145; A61B 17/1215; A61B 17/12159; A61B 17/12163; A61B 17/12168; A61B 17/12172; A61B 17/12177; A61B 17/12181; A61B 17/12186; A61B 17/1219; A61B 17/12195; A61B 2017/00004; A61B 2017/00592; A61B 2017/00597; A61B 2017/22034; A61B 2017/22035; A61B 2017/22079; A61B 2017/2212; A61B 2017/2215; A61B 2017/2217; A61B 2017/12095; A61B 2017/12127; A61M 1/008–0092; A61M 2210/1067; A61M 1/84; A61M 1/90; A61F 2/011; A61F 2/012
See application file for complete search history.

(56) References Cited

U.S. PATENT DOCUMENTS

| | | | |
|---|---|---|---|
| 10,137,037 | B2 | 11/2018 | Tout et al. |
| 10,682,251 | B2 | 6/2020 | Hall et al. |
| 2009/0012558 | A1* | 1/2009 | Chen ................. A61L 27/3604 606/213 |
| 2010/0057013 | A1 | 3/2010 | Harada |
| 2012/0116334 | A1 | 5/2012 | Albert et al. |
| 2015/0250979 | A1 | 9/2015 | Loske |
| 2015/0297807 | A1* | 10/2015 | Leblanc ................. A61M 1/008 600/439 |

FOREIGN PATENT DOCUMENTS

| | | | | |
|---|---|---|---|---|
| CN | 100509079 | C | 7/2009 | |
| CN | 101642381 | A | 2/2010 | |
| CN | 103167885 | A | 6/2013 | |
| CN | 103889477 | A | 6/2014 | |
| CN | 104870029 | A | 8/2015 | |
| DE | 102014224012 | A1 * | 5/2016 | .......... A61M 1/0088 |
| DE | 102014224012 | A1 | 5/2016 | |
| EP | 2769744 | A1 | 8/2014 | |
| EP | 2851102 | A1 * | 3/2015 | ............ A61M 27/00 |
| EP | 2851102 | A1 | 3/2015 | |
| JP | 2013514871 | A | 5/2013 | |
| JP | 2015529117 | A | 10/2015 | |
| RU | 2428208 | C2 | 9/2011 | |
| WO | 2004041346 | A1 | 5/2004 | |

OTHER PUBLICATIONS

International Search Report and Written Opinion for Application No. PCT/EP2017/070649, dated Nov. 2, 2017—11 pages.
Russian Office Action received in Application No. 2019106159/14 dated Oct. 29, 2020, dated 18 pages.
Office Action received in Chinese Application No. 201780053324.3 dated Mar. 16, 2021, with translation, 15 pages.
Office Action received in Japanese Application No. 2019-511605 dated Apr. 13, 2021, with translation, 8 pages.

* cited by examiner

MEDICAL DEVICE, IN PARTICULAR FOR TREATING FISTULAS

RELATED APPLICATION(S)

This application is the United States national phase entry of International Application No. PCT/EP2017/070649, filed Aug. 15, 2017, which claims the benefit of priority of European Application No. 16 186 543.1, filed Aug. 31, 2016. The contents of International Application No. PCT/EP2017/070649 and European Application No. 16 186 543.1 are incorporated by reference herein in their entireties.

FIELD

The present invention relates to a medical device, in particular for treating fistulas, and a medical kit.

BACKGROUND

In medicine, a fistula is an abnormal anastomosis, that is, an abnormal connection between two hollow spaces (technically, two epithelialized surfaces), such as blood vessels, intestines or other hollow organs.

Fistulas are usually caused by injury or surgery, but they can also result from an infection or inflammation. Anal fistula or fistula-in-ano is a chronic abnormal communication between the epithelialized surface of the anal canal and (usually) the perianal skin. An anal fistula can be described as a narrow tunnel with its internal opening in the anal canal and its external opening in the skin near the anus. Anal fistulas commonly occur in people with a history of anal abscesses.

Anal fistulas may have a cryptoglandular origin, i.e. may originate from the anal glands, which are located between the internal and external anal sphincter and drain into the anal canal. If the outlet of these glands becomes blocked, an abscess can form which can eventually extend to the skin surface.

The tract formed by this process is a fistula. It has turned out that in 30% of the cases an abscess, which is a localized infection, develops a fistula.

Alternatively, anal fistulas may have a non-cryptoglandular origin. This type of anal fistula is typically related to other diseases such as tuberculosis, Crohn's disease, lymphogranuloma venereum, actinomycosis and HIV.

Depending on their relationship with the internal and external sphincter muscles, fistulas are classified into the following five categories:

Extrasphincteric fistulas begin at the rectum or sigmoid colon and proceed downward, through the levator ani muscle and open into the skin surrounding the anus.

Suprasphincteric fistulas begin between the internal and external sphincter muscles, extend above and cross the puborectalis muscle, proceed downward between the puborectalis and levator ani muscles, and open an inch or more away from the anus.

Transsphincteric fistulas begin between the internal and external sphincter muscles or behind the anus, cross the external sphincter muscle and open an inch or more away from the anus. They may take a "U" shape and form multiple external openings. This is sometimes termed a "horseshoe fistula".

Intersphincteric fistulas begin between the internal and external sphincter muscles, pass through the internal sphincter muscle, and open very close to the anus.

Submucosal fistulas pass superficially beneath the submucosa and do not cross either sphincter muscle.

In principle, there are several methods available for treating fistulas, in particular anal fistulas.

For example, a drainage seton can be left in place long-term to prevent problems. This is a safe option, although it does not definitively cure fistula.

The treatment "lay-open of fistula-in-ano" involves an operation to cut the fistula open. Once the fistula has been laid open, it will be packed on a daily basis for a short period of time to ensure that the wound heals from the inside out. This option leaves behind a scar, and depending on the position of the fistula in relation to the sphincter muscle, can cause problems with incontinence.

If the fistula is in a high position and it passes through a significant portion of the sphincter muscle, a cutting seton may be used. This involves inserting a thin tube through the fistula tract and tying the ends together outside of the body. The seton is tightened over time, gradually cutting through the sphincter muscle and healing as it goes. This option minimizes scaring, but can also cause incontinence.

A further treatment method is based on the employment of a suture material that is looped through the fistula which keeps it open and allows pus to drain out. In this situation, the seton is referred to as a draining seton. The stitch is placed close to the ano-rectal ring which encourages healing and makes further surgery easy.

Fistulotomy is the surgical opening of a fistulous tract. This can be performed by excision of the tract and surrounding tissue, simple division of the tract, or gradual division and assisted drainage of the tract by means of a seton. A cord is passed through the tract in a loop which is slowly tightened over a period of days or weeks.

A further method, which has been explored in recent years with variable success, involves injecting the fistula with a biodegradable glue such as fibrin which should, in theory, close the fistula from the inside out and let it heal naturally.

A further method involves plugging the fistula with a device made from small intestinal submucosa. The fistula plug is positioned from the inside of the anus with suture.

A further method, the endorectal advancement flap, is a procedure in which the internal opening of the fistula is identified and a flap of mucosal tissue is cut around the opening. The flap is lifted to expose the fistula, which is then cleaned and the internal opening is sewn shut. After cutting the end of the flap on which the internal opening was, the flap is pulled down over the sewn internal opening and sutured in place. The external opening is cleaned and sutured. Success rates are variable and high recurrence rates are directly related to previous attempts to correct the fistula.

The so-called LIFT (ligation of intersphincteric fistula tract) technique is a novel modified approach through the intersphincteric plane for the treatment of fistula-in-ano. The LIFT procedure is based on secure closure of the internal opening and removal of infected cryptoglandular tissue through the intersphincteric approach.

The fistula clip closure is a surgical development, which involves the closure of the internal fistula opening with a superelastic clip made of nitinol. During surgery, the fistula tract is debrided with a special fistula brush and the clip is transanally applied with the aid of a preloaded clip applicator. The surgical principle of this technique relies on the dynamic compression and permanent closure of the internal fistula opening by the superelastic clip. Consequently, the fistula tract dries out and heals instead of being kept open by continuous feeding with stool and fecal organisms.

The PERFACT (proximal superficial cauterization, emptying regularly fistula tracts and curettage of tracts) procedure aims at treating complex and highly complex fistula-in-ano. The procedure is a minimally cutting procedure as both the anal sphincters (internal and external sphincters) are not cut or damaged at all. Therefore, the risk of incontinence is lower in comparison to the surgical procedures as mentioned above. The PERFACT procedure entails two steps: Superficial cauterization of mucosa at and around the internal opening and keeping all the tracts clean. The principle is to permanently close the internal opening by granulation tissue. This is accomplished by superficial electrocauterization at and around the internal opening and subsequently allowing the wound to heal by secondary intention.

Finally, anal fistula can be treated by administering pharmaceutical agents such as antibiotics or cytokines like TNF-α (Tumor Necrosis Factor-α). The reason is that some people will have active infection when they present with a fistula, and this requires clearing up before definitive treatment can be decided.

Though several approaches exist for treating fistulas, so far there is no definitive and in particular no universal treatment available. Often different treatments are combined.

While aggressive treatment bears a high risk of causing incontinence, conservative treatment approaches have a high incidence of recurrences.

A medical product for the drainage of pathological accumulation of fluids is known from EP 2 769 744 A1 and WO 2004/041346 A1.

SUMMARY

Against this backdrop, the problem to be solved by the present invention is to provide a medical device and a medical kit which facilitate gentle as possible treatment of fistulas, in particular anal fistulas, thereby avoiding drawbacks known in the prior art. More preferably, the medical device and the medical kit should facilitate a definitive and in particular universal treatment of fistulas, in particular anal fistulas.

This problem is properly addressed by a medical device and by a medical kit as described herein.

The problem underlying the present invention is further properly addressed by a method for treating a fistula as defined in the description.

The medical device according to the invention is particularly useful for treating a fistula, preferably an anal fistula, in particular a perianal fistula.

More preferably, the medical device is for use in the treatment of a fistula, in particular an anal fistula such as a perianal fistula.

The medical device comprises
a) a fluid collection element,
b) a fluid communication element and
c) a pulling element.

The medical device is in particular characterized in that the pulling element is attached to a distal end of the fluid collection element and/or to a distal end of the fluid communication element.

For the purposes of the present invention, the term "fluid collection element" is to be understood as referring to an element that is capable of taking up, and more preferably, suctioning up and collecting pathological fluids, in particular pathologically accumulated fluids, and preferably to discharging said taken up and collected fluids, as a rule via application of a negative pressure or vacuum, into the fluid communication element.

For the purposes of the present invention, the term "pathological fluids" is to be understood as referring to body fluids such as ichors, exudates, purulent fluids, or intestinal contents. More preferably, the term "pathological fluids" is to be understood as referring to body fluids which are typically present in an abscess and/or fistula.

For the purposes of the present invention, the term "fluid communication element" is to be understood as referring to an element that allows fluid communication to be established between the fluid collection element and a fluid-collecting reservoir such as a fluid collection vessel.

For the purposes of the present invention, the term "proximal end" refers to an end facing toward the trunk of a treating physician, while the term "distal end" refers to an end facing away from the trunk of a treating physician.

For the purposes of the present invention, the term "pulling element" is to be understood as referring to an element that is adapted to place the medical device inside a human or animal body and/or to pull the medical device through a hollow portion of a human or animal body. More preferably, the term "pulling element" is to be understood as referring to an element that is adapted to place the medical device inside a fistula and/or to pull the medical device through a fistula canal.

For the purposes of the present invention, the term "fistula" preferably refers to an anal fistula such as a perianal fistula, in particular selected from the group consisting of extrasphincteric fistula, suprasphincteric fistula, transsphincteric fistula, intersphincteric fistula and submucosal fistula.

The medical device according to the present invention advantageously facilitates a non-invasive treatment of fistulas. Thus, a surgical excision of the fistula canal, which is still the most applied surgical intervention to treat fistulas, in particular anal fistulas, can be circumvented. Thus, any damage to the sphincter muscles leading to fecal incontinence can be prevented.

Attaching the pulling element to the distal end of the fluid collection element and/or to the distal end of the fluid communication element facilitates correct, easy and in particular less traumatic implantation of the medical device inside a fistula and/or correct, easy and in particular less traumatic guidance of the medical device through a fistula canal.

For that purpose, the medical device may be positioned inside a fistula canal and may further be connected to a negative pressure source or vacuum source. Thus, negative pressure and vacuum, respectively may be applied inside the fistula canal. The applied negative pressure and vacuum, respectively advantageously causes the collapse of the canal and promotes the partial growth of scar tissue within the fluid collection element, thereby leading to the healing and closure of the fistula canal.

In a preferred embodiment, as already mentioned above, the pulling element is adapted to place the medical device inside a fistula, in particular an anal fistula, and/or is preferably adapted to pull the medical device through a fistula canal, in particular through a canal of an anal fistula.

In a further embodiment, the pulling element is only attached to the distal end of the fluid collection element.

In a further embodiment, the pulling element is only attached to the distal end of the fluid communication element.

In a further embodiment, the pulling element is attached to the distal end of the fluid collection element and to the distal end of the fluid communication element.

In a further embodiment, the pulling element comprises a loop portion. Advantageously, a loop portion makes it easier to grasp the pulling element, and thus the medical device, for example by the aid of a grasping instrument. Thus, placement of the medical device inside a fistula and/or pull through of the medical device through a fistula canal can be significantly made easier.

Preferably, the loop portion forms a distal end of the pulling element.

The loop portion may have a length from 10 mm to 300 mm, in particular from 15 mm to 100 mm, preferably from 20 mm to 80 mm.

In a further embodiment, the loop portion is formed by means of at least one attachment element.

For the purposes of the invention, the term "at least one" is to be understood as referring to one (singular) or several (plurality), i.e. two or more. For example, the term "at least one attachment element" is to be understood as referring to one attachment element or several attachment elements, i.e. two or more attachment elements.

The at least one attachment element is preferably selected from the group consisting of at least one knot, at least one thread such as at least one suture, at least one wire, at least one clip, at least one material bonding engagement such as at least one glue or at least one weld, in particular at least one vibration weld or thermal weld, and combinations of at least two of said attachment elements.

More preferably, the loop portion is formed by means of at least one knot of the pulling element. In other words, more preferably, the loop portion is formed by knotting the pulling element.

In a further embodiment, the pulling element comprises a non-looped portion.

Preferably, the non-looped portion forms a proximal end of the pulling element.

The non-looped portion may have a length from 50 mm to 400 mm, in particular from 100 mm to 300 mm, preferably from 150 mm to 250 mm.

In a further embodiment, the pulling element may comprise a loop portion and/or a non-looped portion. Preferably, the pulling element comprises a loop portion and a non-looped portion.

In a further embodiment, the pulling element is attached to the distal end of the fluid collection element and/or to the distal end of the fluid communication element via the non-looped portion.

In a further embodiment, at the distal end of the fluid collection element the pulling element penetrates a structure, in particular a porous or foam structure, preferably an open cell structure, of the fluid collection element.

In a further embodiment, the pulling element engages at least one hole and/or at least one perforation that are arranged on a distal portion of the fluid communication element. Thus, a secure attachment of the pulling element to the fluid collection element and/or fluid communication element can be accomplished.

In particular, the pulling element engages several holes and/or several perforations that are arranged along a distal portion of the fluid communication element. Thus, an especially secure attachment of the pulling element to the fluid collection element and/or fluid communication element can be accomplished.

In a further embodiment, the pulling element is attached to the distal end of the fluid collection element and/or of the fluid communication element by means of at least one attachment element that is preferably selected from the group consisting of at least one knot, at least one thread such as at least one suture, at least one wire, at least one clip and/or by means of at least one material bonding engagement such as at least one glue, or at least one weld, in particular at least one vibration weld or thermal weld.

In a further embodiment, the pulling element is attached to the distal end of the fluid collection element and/or to the distal end of the fluid communication element by means of knotting. According to an especially preferred embodiment, the pulling element is knotted over the distal end of the fluid collection element and/or of the fluid communication element.

In a further embodiment, the pulling element is attached to the distal end of the fluid collection element and/or to the distal end of the fluid communication element by means of stitching.

In a further embodiment, the pulling element is attached to the distal end of the fluid collection element and/or to the distal end of the fluid communication element by means of sewing.

In a further embodiment, the pulling element is attached to the distal end of the fluid collection element and/or to the distal end of the fluid communication element by means of clipping.

In a further embodiment, the pulling element is attached to the distal end of the fluid collection element and/or to the distal end of the fluid communication element by means of molding such as injection molding.

In a further embodiment, the pulling element is attached to the distal end of the fluid collection element and/or to the distal end of the fluid communication element by means of a material bonding engagement.

The material bonding engagement is preferably selected from the group consisting of gluing and welding such as vibration welding or thermal welding.

In a further embodiment, the pulling element is a longitudinal, in particular filamentary, element.

The pulling element may have a length from 50 mm to 400 mm, in particular from 100 mm to 300 mm, preferably from 150 mm to 250 mm.

In principle, the pulling element may be a wire or thread, in particular a monofilament, pseudo monofilament or multifilament, i.e. a multiple thread. Under atraumatic or at least less traumatic circumstances, a pulling element being configured as a thread is more preferably.

According to an especially preferred embodiment, the pulling element is a multifilament, in particular a twisted or braided multifilament, more preferably a braided multifilament. Thus, the pulling element advantageously exhibits sufficient flexible characteristics which facilitates handling of the medical device, in particular placement of the medical device inside a fistula and/or pull through of the medical device through a fistula canal.

In a further embodiment, the pulling element comprises an in vivo degradable or in vivo resorbable material. Particularly, the pulling element may consist of an in vivo degradable or in vivo resorbable material.

For the purposes of the present invention, the term "in vivo degradable material" is to be understood as referring to a material which is decomposed in a human or animal body, in particular under the influence of enzymes. The decomposition of the material may occur completely until mineralization, i.e. release of chemical elements and their incorporation into inorganic compounds, such as carbon dioxide, oxygen and/or ammonia, or may stop at the stage of intermediate products which are stable towards further decomposition.

For the purposes of the present invention, the term "in vivo resorbable material" is to be understood as referring to a material which is absorbed in a human or animal body by living cells or living tissue such as kidneys without decomposition or without essential decomposition of the material.

The in vivo degradable or in vivo resorbable material may be selected from the group consisting of polyvinyl alcohol, polyhydroxyalkanoate, polyglycolide, polylactide, polydioxanone, poly-3-hydroxybutyrate, poly-4-hydroxybutyrate, polytrimethylene carbonate, poly-ε-caprolactone, copolymers of at least two of said polymers such as poly(lactid-co-glycolide) and mixtures (blends) of at least two of said polymers.

For the purposes of the present invention, the term "copolymer" is to be understood as referring to a polymer which is composed of at least two different monomer units. Accordingly, the term "copolymer" may encompass bipolymers, terpolymers, tetrapolymers and the like.

An especially preferred in vivo degradable or in vivo resorbable material is a terpolymer, in particular a triblock terpolymer, composed of glycolide units, trimethylene carbonate units and ε-caprolactone units. Such a terpolymer is commercially available under the name Monosyn®.

In a further embodiment, the pulling element comprises an in vivo non-degradable or in vivo non-resorbable material. Particularly, the pulling element may consist of an in vivo non-degradable or in vivo non-resorbable material.

The in vivo non-degradable or in vivo non-resorbable material may be selected from the group consisting of polyolefin, polyester, polyamide, polyurethane, elastomer such as thermoplastic elastomer, polyetherketone, organic polysulfide, copolymers of at least two of said polymers and mixtures (blends) of at least two of said polymers.

The polyolefin may be selected from the group consisting of polyethylene, low-density polyethylene, high-density polyethylene, high-molecular-weight polyethylene, ultra-high-molecular-weight polyethylene, polypropylene, polytetrafluorethylene, polyvinylidene fluoride, polyvinylidene chloride, polytetrafluorpropylene, polyhexafluorpropylene, copolymers of at least two of said polyolefins and mixtures (blends) of at least two of said polyolefins.

The polyester may be selected from the group consisting of polyethylene terephthalate, polypropylene terephthalate, polybutylene terephthalate, copolymers of at least two of said polyesters and mixtures (blends) of at least two of said polyesters.

The polyamide may be selected from the group consisting of polyamide 6 (polymer of ε-caprolactam- or omega-aminocaproic acid units), polyamide 66 (polymer of hexamethylenediamine units and adipic acid units), polyamide 69 (polymer of hexamethylenediamine units and azelaic acid units), polyamide 612 (polymer of hexamethylenediamine units and dodecanedioic acid units), polyamide 11 (polymer of 11-aminoundecanoic acid units), polyamide 12 (polymer of laurolactam acid units and omega-aminododecanoic acid units), polyamide 46 (polymer of tetramethylenediamine units and adipic acid units), polyamide 1212 (polymer of dodecandiamine units and dodecanedioic acid units), polyamide 6/12 (polymer of caprolactam units and laurolactam units), polyamide 66/610 (polymer of hexamethylenediamine units, adipic acid units and sebacic acid units), copolymers of at least two of said polyamides and mixtures (blends) of at least two of said polyamides.

The polyurethane may be selected from the group consisting of aliphatic polycarbonate urethane, silicon polycarbonate urethane, polyether urethane, silicone polyether urethane, polyurethane ether, copolymers of at least two of said polyurethanes and mixtures (blends) of at least two of said polyurethanes.

The thermoplastic elastomer may be selected from the group consisting of thermoplastic copolyamide, thermoplastic polyester elastomer, thermoplastic copolyester, thermoplastic elastomer on olefin basis, styrene block copolymer, thermoplastic elastomer on urethane basis, crosslinked thermoplastic elastomer on olefin basis, copolymers of at least two of said elastomers and mixtures (blends) of at least two of said elastomers.

The polyetherketone may be selected from the group consisting of polyetherketoneketone, polyetheretheretherketone, polyetherketoneketone, polyetherketoneetherketoneketone, copolymers of at least two of said polyetherketones and mixtures (blends) of at least two of said polyetherketones.

In a further embodiment, the fluid communication element has a tubular shape. In other words, according to a further embodiment, the fluid communication element is a tube, in particular a plastic tube, preferably a flexible plastic tube. More preferably, the fluid communication element is a drainage tube, in particular a redon drainage tube.

In a further embodiment, the fluid communication element is a catheter.

In a further embodiment, the fluid communication element has a round cross-section, in particular a circular or oval cross-section.

In an alternative embodiment, the fluid communication element has a non round cross-section, in particular a polygonal cross-section. For example, the fluid communication element may have a triangular, rectangular, square, trapezoid, rhomboid, pentagonal, hexagonal, heptagonal, octagonal, nonagonal, decagonal or star-like cross-section.

In a further embodiment, the fluid communication element has an outer diameter from 0.5 mm to 15 mm, in particular 1 mm to 5 mm, preferably 1.2 mm to 3 mm.

In a further embodiment, the fluid communication element has an inner diameter from 0.1 mm to 13 mm, in particular 0.2 mm to 4 mm, preferably 0.5 mm to 2 mm.

In a further embodiment, the fluid communication element has a length from 200 mm to 1000 mm, in particular 300 mm to 800 mm, preferably 350 mm to 600 mm.

In a further embodiment, the fluid communication element comprises a flexible material or is made of a flexible material.

Principally, the fluid communication element may comprise an in vivo degradable or in vivo resorbable material or may consist of an in vivo degradable or in vivo resorbable material.

However, it is preferred that the fluid communication comprises an in vivo non-degradable or in vivo non-resorbable material or consists of an in vivo non-degradable or in vivo non-resorbable material More preferably, the fluid communication element comprises a material or consists of a material which is selected from the group consisting of polyethylene, polypropylene, polyvinyl chloride, polyurethane, silicone, polytetrafluorethylene, copolymers of at least two of said polymers and mixtures (blends) of at least two of said polymers.

In a further embodiment, at least one portion of the fluid communication element is arranged inside the fluid collection element, preferably inside an inner canal of the fluid collection element.

More preferably, a distal portion, in particular only a distal portion, of the fluid communication element is arranged inside the fluid collection element, preferably inside an inner canal of the fluid collection element. In other words, more preferably a distal portion, in particular only a distal portion, of the fluid communication element is surrounded or engirded by the fluid collection element. The distal portion may have a length from 10 mm to 250 mm, in particular 50 mm to 200 mm, preferably 80 mm to 150 mm.

In a further embodiment, the fluid communication element, in particular the distal portion of the fluid communication element, comprises holes and/or perforations. Expediently, the holes and/or perforations are configured as breakthroughs, i.e. as holes and/or perforations breaking through the wall of the communication element.

The holes and/or perforations advantageously facilitate transfer of body liquids, which have been taken up by the fluid collection element, into the fluid communication element.

Preferably, the holes and/or perforations are arranged along, i.e. in the longitudinal direction, of the fluid communication element, in particular the distal portion of the fluid communication element.

The holes and/or perforations may have a mutual distance of 1 mm to 20 mm, in particular 2 mm to 10 mm, preferably 3 mm to 8 mm.

The holes and/or perforations may have a round, in particular circular or oval, cross-section.

Alternatively, the holes and/or perforations may have a non-round, in particular polygonal, cross-section. For example, the holes and/or perforations may have a triangular, square, rectangular, trapezoid, rhomboid, pentagonal, hexagonal, heptagonal, octagonal, nonagonal, decagonal or star-like cross-section.

Further, the holes and/or perforations may have a diameter from 0.1 mm to 5 mm, in particular 0.3 mm to 4 mm, preferably 0.5 mm to 3 mm.

Further, the holes and/or perforations may have a length from 10 mm to 250 mm, in particular 50 mm to 200 mm, preferably 80 mm to 150 mm.

In a further embodiment, the fluid communication element comprises a connector, in particular a luer-lock connector, preferably a male Luer-lock connector.

The connector is preferably a negative pressure or vacuum connector, i.e. a connector that is adapted to attach a proximal end of the fluid communication element to an extension tube and/or to a negative pressure or vacuum source, in particular a digital negative pressure or vacuum source. The negative pressure and vacuum source, respectively may be a negative pressure and vacuum pump, respectively.

Preferably, the connector is attached to a proximal end of the fluid communication element.

For the purposes of the present invention, the term "extension tube" is to be understood as referring to a tube that connects the fluid communication element to a negative pressure or vacuum source, in particular to a digital negative pressure or vacuum source.

In a further embodiment, the fluid collection element comprises an in vivo degradable or in vivo resorbable material. Particularly, the fluid collection element may consist of an in vivo degradable material or of an in vivo resorbable material.

The in vivo degradable or in vivo resorbable material may be selected from the group consisting of polyvinyl alcohol, polyhydroxyalkanoate, polyglycolide, polylactide, polydioxanone, poly-3-hydroxybutyrate, poly-4-hydroxybutyrate, polytrimethylene carbonate, poly-ε-caprolactone, copolymers of at least two of said polymers such as poly(lactid-co-glycolide) and mixtures (blends) of at least two of said polymers.

In a further embodiment, the fluid collection element comprises an in vivo non-degradable or in vivo non-resorbable material. Particularly, the fluid collection element may consist of an in vivo non-degradable or in vivo non-resorbable material.

The in vivo non-degradable or in vivo non-resorbable material may be selected from the group consisting of polyolefin, polyester, polyamide, polyurethane, elastomer such as thermoplastic elastomer, polyetherketone, organic polysulfide, copolymers of at least two of said polymers and mixtures (blends) of at least two of said polymers.

The polyolefin may be selected from the group consisting of polyethylene, low-density polyethylene, high-density polyethylene, high-molecular-weight polyethylene, ultra-high-molecular-weight polyethylene, polypropylene, polytetrafluorethylene, polyvinylidene fluoride, polyvinylidene chloride, polytetrafluorpropylene, polyhexafluorpropylene, copolymers of at least two of said polyolefins and mixtures (blends) of at least two of said polyolefins.

The polyester may be selected from the group consisting of polyethylene terephthalate, polypropylene terephthalate, polybutylene terephthalate, copolymers of at least two of said polyesters and mixtures (blends) of at least two of said polyesters.

The polyamide may be selected from the group consisting of polyamide 6 (polymer of ε-caprolactam- or omega-aminocaproic acid units), polyamide 66 (polymer of hexamethylenediamine units and adipic acid units), polyamide 69 (polymer of hexamethylenediamine units and azelaic acid units), polyamide 612 (polymer of hexamethylenediamine units and dodecanedioic acid units), polyamide 11 (polymer of 11-aminoundecanoic acid units), polyamide 12 (polymer of laurolactam acid units and omega-aminododecanoic acid units), polyamide 46 (polymer of tetramethylenediamine units and adipic acid units), polyamide 1212 (polymer of dodecandiamine units and dodecanedioic acid units), polyamide 6/12 (polymer of caprolactam units and laurolactam units), polyamide 66/610 (polymer of hexamethylenediamine units, adipic acid units and sebacic acid units), copolymers of at least two of said polyamides and mixtures (blends) of at least two of said polyamides.

The polyurethane may be selected from the group consisting of aliphatic polycarbonate urethane, silicon polycarbonate urethane, polyether urethane, silicone polyether urethane, polyurethane ether, copolymers of at least two of said polyurethanes and mixtures (blends) of at least two of said polyurethanes.

The thermoplastic elastomer may be selected from the group consisting of thermoplastic copolyamide, thermoplastic polyester elastomer, thermoplastic copolyester, thermoplastic elastomer on olefin basis, styrene block copolymer, thermoplastic elastomer on urethane basis, crosslinked thermoplastic elastomer on olefin basis, copolymers of at least two of said elastomers and mixtures (blends) of at least two of said elastomers.

The polyetherketone may be selected from the group consisting of polyetherketoneketone, polyetheretheretherketone, polyetheretherketoneketone, polyetherketoneetherketoneketone, copolymers of at least two of said polyetherketones and mixtures (blends) of at least two of said polyetherketones.

In a further embodiment, the fluid collection element has a non-textile structure.

Preferably, the fluid collection element has a foam structure, in particular an open-cell foam structure.

In a further embodiment, the fluid collection element has a porous structure.

In a further embodiment, the fluid collection element comprises a linear pore density of 3 pores per cm to 30 pores per cm, in particular 3 pores per cm to 25 pores per cm, preferably 3 pores per cm to 20 pores per cm. For the purposes of the present invention, the term "linear pore density" is to be understood as referring to pores which are arranged successively, i.e. in a row.

In a further embodiment, the fluid collection element has a sponge structure, in particular an open-cell or porous sponge structure.

According to an especially preferred embodiment, the fluid collection element has an open-cell foam structure made of polyurethane. As regards useful polyurethanes, reference is also made in its entirety to the previous description.

In a further embodiment, the fluid collection element has a textile structure, in particular a mesh structure, preferably a rolled mesh structure.

According to an especially preferred embodiment, the fluid collection element has a rolled mesh structure made of a polyolefin, preferably made of polypropylene.

In a further embodiment, the fluid collection element has a grid or grid-like structure.

In a further embodiment, the fluid collection element comprises flock fibers. In other words, according to a further embodiment, the fluid collection element may be configured as a flocked element. As regards useful materials for the flock fibers, reference is made to the materials mentioned in the previous description.

In a further embodiment, the fluid collection element has a ceramic structure.

In a further embodiment, the fluid collection element is configured as a rubber element, in particular as a perforated rubber element.

In a further embodiment, the fluid collection element is configured as a flexible tube, in particular perforated flexible tube.

In principle, the fluid collection element may be of any shape which allows placement of the medical device into a fistula canal, and/or which allows pull through of the medical device through a fistula canal.

More specifically, the fluid collection element may have a polyhedral or non-polyhedral shape. For example, the fluid collection element may have the form of a cube, cuboid, prism, such as cylinder, pyramid, cone or ball.

Further, the fluid collection element may have a round, in particular circular or oval, cross-section.

Alternatively, the fluid collection element may have a non-round cross-section. For example, the fluid collection element may have a triangular, rectangular, square, trapezoid, rhomboid, pentagonal, hexagonal, heptagonal, octagonal, nonagonal, decagonal or star-like cross-section.

In a preferred embodiment, the fluid collection element has a cylindrical shape.

As mentioned above, it is preferably that the fluid collection element comprises a canal, in particular an inner canal.

Preferably, the canal extends along, i.e. in the longitudinal direction, of the fluid collection element. The canal may have an inner diameter from 0.5 mm to 15 mm, in particular 1 mm to 5 mm, preferably 1.2 mm to 3 mm.

The canal of the fluid collection element may have a round cross-section, in particular a circular or oval cross-section.

Alternatively, the canal of the fluid collection element may have a non round cross-section, in particular a triangular, rectangular, square, trapezoid, rhomboid, pentagonal, hexagonal, heptagonal, octagonal, nonagonal, decagonal or star-like cross-section.

In a further embodiment, the fluid collection element comprises a longitudinal cut, in particular made by means of a punch or a cross-section die. In particular, the longitudinal cut can be a slot.

In a further embodiment, the fluid collection element has an outer diameter from 3 mm to 30 mm, in particular 5 mm to 20 mm, preferably 8 mm to 15 mm.

In a further embodiment, the fluid collection element, in particular the canal, may have a length from 10 mm to 250 mm, in particular 50 mm to 200 mm, preferably 80 mm to 150 mm.

In a further embodiment, the fluid collection element is attached to the fluid communication element, in particular to an outer surface of the fluid communication element, preferably by means of at least one attachment element.

More preferably, the fluid collection element is attached to a distal portion of the fluid communication element, in particular to an outer surface of a distal portion of the fluid communication element, preferably by means of at least one attachment element.

In a further embodiment, the fluid collection element may be attached to the fluid communication element, in particular to a distal portion of the fluid communication element, by means of at least one attachment element, in particular by means of at least one thread such as at least one monofilament, at least one pseudo monofilament or at least one multifilament, at least one knotted thread such as at least one knotted monofilament, at least one knotted pseudo monofilament or at least one knotted multifilament, at least one wire, at least one clip or at least on material bonding engagement such as at least one glue or at least one weld, particularly at least one vibration weld or thermal weld.

In particular, the fluid collection element may be attached to the fluid communication element, in particular to a distal portion of the fluid communication element, by means of knotting, stitching, sewing, clipping, molding or material bonding engagement, such as gluing, welding, in particular vibration welding or thermal welding, and the like.

The at least one attachment element preferably penetrates through a structure, in particular a foam or sponge structure, preferably an open-cell foam or sponge structure, of the fluid collection element.

Preferably, the at least one attachment element engages at least one hole and/or at least one perforation of the fluid communication element.

In a further embodiment, the at least one attachment element is at least one thread, in particular at least one knotted thread.

In a further embodiment, the at least one attachment element comprises an in vivo degradable or in vivo resorbable material. Particularly, the at least one attachment element may consist of an in vivo degradable material or of an in vivo resorbable material.

The in vivo degradable or in vivo resorbable material may be selected from the group consisting of polyvinyl alcohol, polyhydroxyalkanoate, polyglycolide, polylactide, polydioxanone, poly-3-hydroxybutyrate, poly-4-hydroxybutyrate, polytrimethylene carbonate, poly-ε-caprolactone, copolymers of at least two of said polymers such as poly(lactid-co-glycolide) and mixtures (blends) of at least two of said polymers.

In a further embodiment, the at least one attachment element comprises an in vivo non-degradable or in vivo non-resorbable material. Particularly, the fluid collection element may consist of an in vivo non-degradable or in vivo non-resorbable material.

The in vivo non-degradable or in vivo non-resorbable material may be selected from the group consisting of polyolefin, polyester, polyamide, polyurethane, elastomer such as thermoplastic elastomer, polyetherketone, organic polysulfide, copolymers of at least two of said polymers and mixtures (blends) of at least two of said polymers.

The polyolefin may be selected from the group consisting of polyethylene, low-density polyethylene, high-density polyethylene, high-molecular-weight polyethylene, ultra-high-molecular-weight polyethylene, polypropylene, polytetrafluorethylene, polyvinylidene fluoride, polyvinylidene chloride, polytetrafluorpropylene, polyhexafluorpropylene, copolymers of at least two of said polyolefins and mixtures (blends) of at least two of said polyolefins.

The polyester may be selected from the group consisting of polyethylene terephthalate, polypropylene terephthalate, polybutylene terephthalate, copolymers of at least two of said polyesters and mixtures (blends) of at least two of said polyesters.

The polyamide may be selected from the group consisting of polyamide 6 (polymer of ε-caprolactam- or omega-aminocaproic acid units), polyamide 66 (polymer of hexamethylenediamine units and adipic acid units), polyamide 69 (polymer of hexamethylenediamine units and azelaic acid units), polyamide 612 (polymer of hexamethylenediamine units and dodecanedioic acid units), polyamide 11 (polymer of 11-aminoundecanoic acid units), polyamide 12 (polymer of laurolactam acid units and omega-aminododecanoic acid units), polyamide 46 (polymer of tetramethylenediamine units and adipic acid units), polyamide 1212 (polymer of dodecandiamine units and dodecanedioic acid units), polyamide 6/12 (polymer of caprolactam units and laurolactam units), polyamide 66/610 (polymer of hexamethylenediamine units, adipic acid units and sebacic acid units), copolymers of at least two of said polyamides and mixtures (blends) of at least two of said polyamides.

The polyurethane may be selected from the group consisting of aliphatic polycarbonate urethane, silicon polycarbonate urethane, polyether urethane, silicone polyether urethane, polyurethane ether, copolymers of at least two of said polyurethanes and mixtures (blends) of at least two of said polyurethanes.

The thermoplastic elastomer may be selected from the group consisting of thermoplastic copolyamide, thermoplastic polyester elastomer, thermoplastic copolyester, thermoplastic elastomer on olefin basis, styrene block copolymer, thermoplastic elastomer on urethane basis, crosslinked thermoplastic elastomer on olefin basis, copolymers of at least two of said elastomers and mixtures (blends) of at least two of said elastomers.

The polyetherketone may be selected from the group consisting of polyetherketoneketone, polyetheretherketone, polyetheretherketoneketone, polyetherketoneetherketoneketone, copolymers of at least two of said polyetherketones and mixtures (blends) of at least two of said polyetherketones.

In a further embodiment, the at least one attachment element may comprise a different material, in particular a different in vivo degradable or in vivo resorbable material or a different in vivo non-degradable or in vivo-non resorbable material, than the pulling element. Particularly, the at least one attachment element may consist of a different material, in particular a different in vivo degradable or in vivo resorbable material or a different in vivo non-degradable or in vivo-non resorbable material, than the pulling element. As regards useful materials, reference is made in its entirety to the previous description.

In a further embodiment, the at least one attachment element may comprise the same material, in particular the same in vivo degradable or in vivo resorbable material or the same in vivo non-degradable or in vivo-non resorbable material, like the pulling element. Particularly, the at least one attachment element may consist of the same material, in particular the same in vivo degradable or in vivo resorbable material or the same in vivo non-degradable or in vivo-non resorbable material, like the pulling element. As regards useful materials, reference is made in its entirety to the previous description.

In a further embodiment, the fluid collection element is attached to the fluid communication element, in particular to a distal portion of the fluid communication element, by means of several attachment elements, for example by means of 2 to 6 attachment elements.

Preferably, the attachment elements are arranged along, i.e. in the longitudinal direction, of the fluid collection element.

In particular, the attachment elements may have a mutual distance from 10 mm to 200 mm, in particular 25 mm to 100 mm, preferably 25 mm to 50 mm, along the fluid collection element.

The attachment elements are preferably threads, in particular knotted threads.

In a further embodiment, the attachment elements each may comprise a different material, in particular a different in vivo degradable or in vivo resorbable material or a different in vivo non-degradable or in vivo-non resorbable material. Particularly, the attachment elements each may consist of a different material, in particular a different in vivo degradable or in vivo resorbable material or a different in vivo non-degradable or in vivo-non resorbable material. As regards useful materials, reference is made in its entirety to the previous description.

In a further embodiment, the attachment elements each may comprise the same material, in particular the same in vivo degradable or in vivo resorbable material or the same in vivo non-degradable or in vivo-non resorbable material. Particularly, the attachment elements each may consist of the same material, in particular the same in vivo degradable or in vivo resorbable material or the same in vivo non-degradable or in vivo-non resorbable material. As regards useful materials, reference is also made in its entirety to the previous description.

In a further embodiment, the medical device, in particular the fluid collection element, may comprise an additive, in particular a biological or pharmaceutical agent, preferably selected from the group consisting of antimicrobial and preferably antibiotic, agent, antiseptic agent, disinfecting agent, anti-inflammatory agent, odor-inhibiting agent and mixtures of at least two of said agents.

In a further embodiment, the fluid collection element comprises a lubricant. More preferably, the fluid collection element is impregnated with a lubricant.

The lubricant may be selected from the group consisting of medical water-soluble hydrogels, petroleum jelly, silicon based lubricant and mixtures of at least two of said lubricants.

The medical device according to the present invention is preferably provided for vacuum therapy of a fistula, in particular an anal fistula such as a perianal fistula.

More preferably, the medical device according to the present invention is for use in vacuum therapy of a fistula, in particular an anal fistula such as a perianal fistula.

In a further embodiment, the medical device is an implant.

According to a second aspect, the present invention relates to a medical kit, preferably for treating a fistula, in particular an anal fistula such as a perianal fistula.

Preferably, the medical kit is for use in the treatment of a fistula, in particular an anal fistula such as a perianal fistula.

More preferably, the medical kit is for use in vacuum therapy of a fistula, in particular an anal fistula such as a perianal fistula.

The kit comprises a medical device comprising
a) a fluid collection element,
b) a fluid communication element and
c) a pulling element.

The medical device is in particular characterized in that the pulling element is attached to a distal end of the fluid collection element and/or to a distal end of the fluid communication element.

Further, the kit comprises at least one component which is preferably selected from the group consisting of negative pressure or vacuum source, fluid collection vessel, extension tube, sterile filter, grasping instrument, lubricant, syringe, suture, sealing patch, scissors and stapler.

The negative pressure or vacuum source is preferably configured as a pump.

Further it is preferred that the negative pressure or vacuum source is adapted to produce negative pressure of 20 mmHg to 700 mmHg, in particular 30 mmHg to 300 mmHg, preferably 50 mmHg to 250 mmHg.

As regards further features and advantages of the medical kit, in particular of the medical device, reference is made in its entirety to the embodiments described in the context of the first aspect of the invention.

According to a third aspect, the present invention relates to a method for treating a fistula, in particular an anal fistula such as a perianal fistula.

The method comprises the step of placing a medical device inside a fistula, wherein the medical device comprises
a) a fluid collection element,
b) a fluid communication element and
c) a pulling element, wherein the pulling element is attached to a distal end of the fluid collection element and/or of the fluid communication element.

In a further embodiment, placement of the medical device is achieved by means of a grasping instrument (grasper). The grasping instrument is expediently adapted to pull the pulling element, and thus the medical device inside the fistula.

In a further embodiment, the method comprises the further step of trimming the fluid collection element. Thus, the size of the fluid collection element can be advantageously adapted to the specific size of a patient's fistula.

In a further embodiment, the method comprises the further step of sealing the opposing ends of the fistula. Sealing the ends of the fistula can be, by way of example, achieved by means of suturing, stapling or patch coverage. If the fistula is an anal fistula, the rectal opening may be sutured or stapled, while the skin opening may be sealed by the aid of a patch.

In a further embodiment, the method comprises the further step of connecting the fluid communication element, in particular via an extension tube, to a negative pressure or vacuum source, in particular to a negative pressure or vacuum pump.

In a further embodiment, a negative pressure or vacuum is applied. By way of example, a negative pressure or vacuum of 20 mmHg to 700 mmHg, in particular 30 mmHg to 300 mmHg, preferably 50 mmHg to 250 mmHg, is applied.

In a further embodiment, the negative pressure or vacuum is applied for 1 day to 31 days, in particular 1 day to 7 days, preferably 1 day to 5 days.

In a further embodiment, the method comprises the further step of removing the medical device from the fistula after the treatment has been finished. In case of long treatments where the device needs to be replaced by a new one, it has to be considered that the rectal part of the fistula is typically already closed (e.g. sutured or stapled). In this specific case, the portion of the distal end of the medical device (including the pulling element) can be trimmed and discarded in order to adapt the size of the fluid collection element to the size of the fistula. After trimming, the fluid collection element and the fluid communication element can be implanted, in particular by means of a grasping instrument (grasper or tweezer) expediently adapted to hold and push the medical device through the fistula canal.

Further characteristics and advantages of the invention are given in the following description of preferred embodiments in the form of examples, figures, and figure descriptions. These may concern individual embodiments of characteristics or embodiments combining several characteristics. The embodiments described serve only to explain the present invention, which is by no means limited to said embodiments.

DETAILED DESCRIPTION

Figure 1:
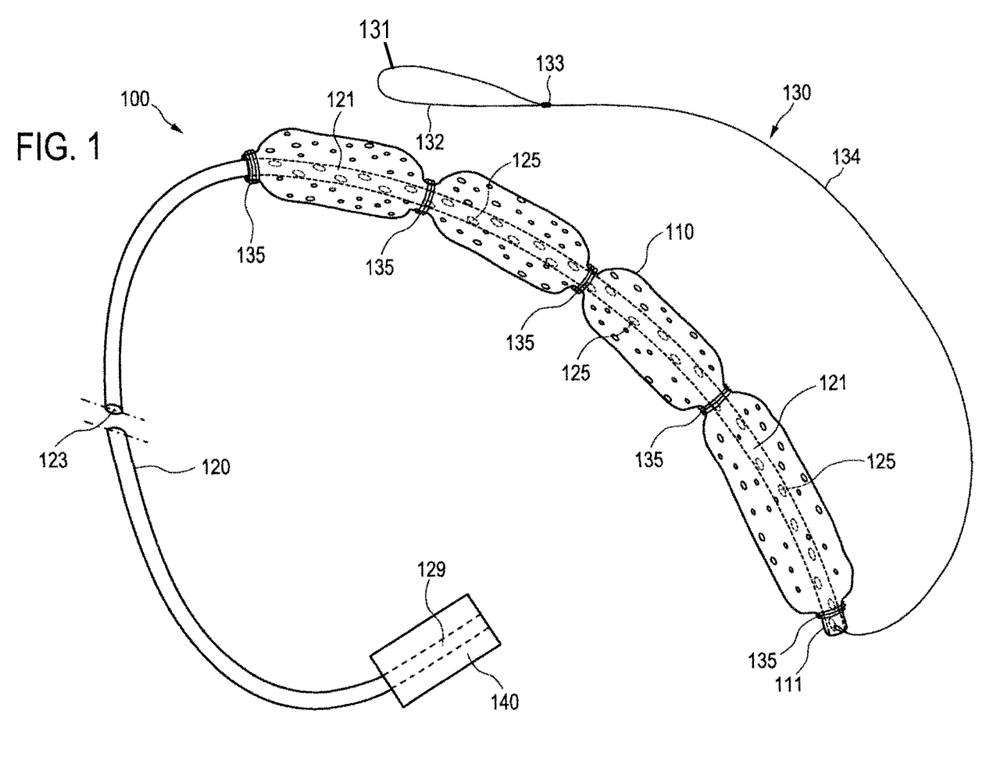
FIG. 1: an embodiment of a medical device according the present invention and
FIG. 2a-d treatment of an anal fistula by means of a medical device according to the present invention.

FIG. 1 schematically shows a medical device 100 according to the present invention.

The medical device comprises a fluid collection element 110, a fluid communication element 120 and a pulling element 130.

The fluid collection element 110 may have a foam structure, in particular an open-cell foam structure, preferably made of polyurethane.

The fluid communication element 120 has a tubular shape and is preferably configured as a drainage tube.

The pulling element 130 is preferably configured as a thread, in particular as a multiple thread, i.e. multifilament. More preferably, the pulling element 130 may be a braided multifilament. For example, the pulling element 130 may be a braided polyethylene terephthalate thread.

The pulling element 130 comprises a loop portion 132 and a non-looped portion 134. The loop portion 132 is preferably formed by an attachment element 133, in particular knot.

While the loop portion 132 is arranged at a distal end 131 of the pulling element 130, the pulling element is attached via its non-looped portion 134 to the distal end 111 of the fluid collection element 110. Preferably, the pulling element 130 is attached to the distal end 111 of the fluid collection element 110 by means of knotting knot, preferably of the pulling element 130. In other words, it is preferred that the pulling element 130 is knotted over the distal end 111.

Advantageously, the pulling element 130 facilitates guidance of the medical device 100 through a fistula canal.

The fluid collection element 110 may be attached to the fluid communication element 130 several attachment elements 135, in particular in the form of knots. The attachment elements 135 may constrict the fluid collection element 110 at the respective fixation sites. Advantageously, the attachment elements 135 effect connection between the fluid collection element 110 and the fluid communication element 120. Further, the medical device 100 can better withstand the forces exerted during the introduction and removal of the medical device 100, if the medical device 100 comprises several attachment elements 135.

Preferably, the fluid collection element 110 serves the purpose to prevent the fluid communication element 120 form being clogged when negative pressure or vacuum is applied.

Furthermore, the fluid collection element 110 advantageously distributes the pressure through the length of a fistula canal, once negative pressure or vacuum is applied.

Furthermore, a porosity or open cell structure of the fluid collection element 110 in combination with a negative pressure or vacuum supplied through the fluid communication element 120 may advantageously enable and/or promote tissue in-growth and liquid collection.

Preferably, only a distal portion 121 of the fluid communication element 120 is engirded by the fluid collection element 110.

In order to allow transfer of body liquids taken up by the fluid collection element 110 into the fluid communication element 120, in particular into a canal 123 of the fluid communication element, the distal portion 121 comprises several holes 125. Alternatively or additionally, the distal portion 121 may comprise several perforations. Typically, the holes 125 are arranged along the distal portion 121. Advantageously, the holes 125 prevent the fluid communication element 120 from being blocked once vacuum is applied.

Typically, the fluid communication element 120 is adapted to conduct a negative pressure or vacuum to a fistula canal.

Further, a connector 140, in particular a luer-lock connector, may be attached to the proximal end 129 of the fluid communication element. The connector 140 is preferably adapted to connect the fluid communication element 120 to an extension tube (not shown). The extension tube is typically adapted to facilitate connection with a negative pressure or vacuum pump.

Figure 2A:
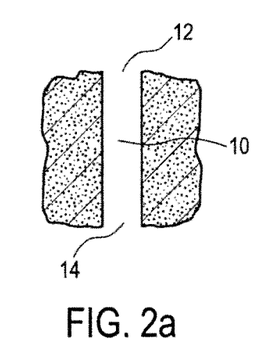

FIG. 2a schematically shows an anal fistula 10. The fistula 10 is featured by a skin opening 12 and a rectal opening 14.

Figure 2B:
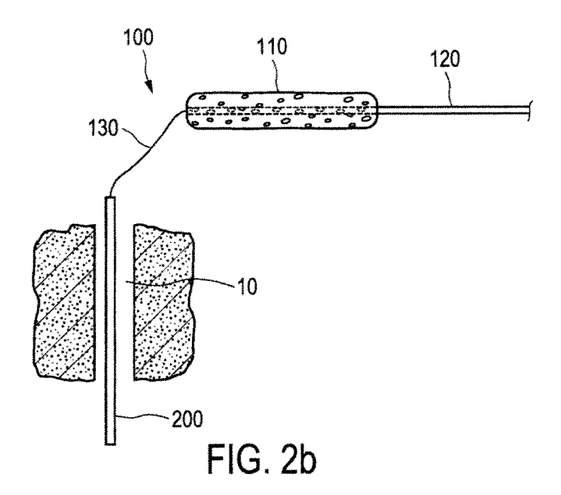
Figure 2C:
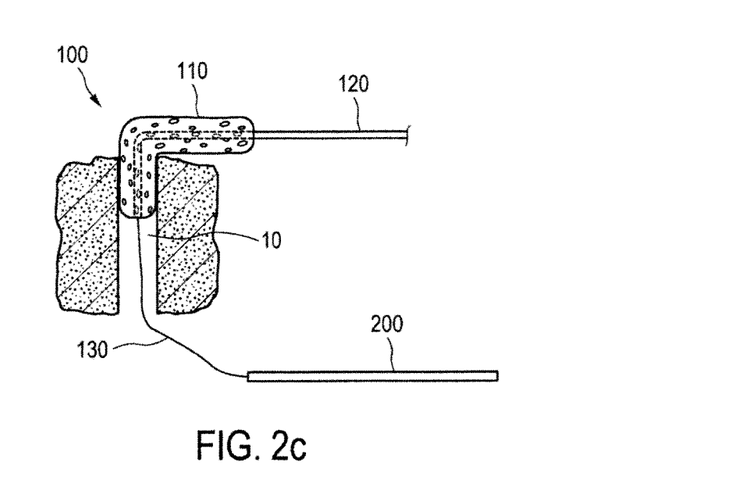

To treat the anal fistula 10, a medical device 100 according to the present invention is placed inside the fistula 10. The medical device 100 comprises a fluid collection element 110, a fluid communication 120 and a pulling element 130. The placement of the medical device 100 inside the fistula 10 is expediently achieved by means of a grasping device 200 (see FIG. 2b). Thus, the medical device 100 can be placed inside the fistula 10 (see FIG. 2c).

Figure 2D:
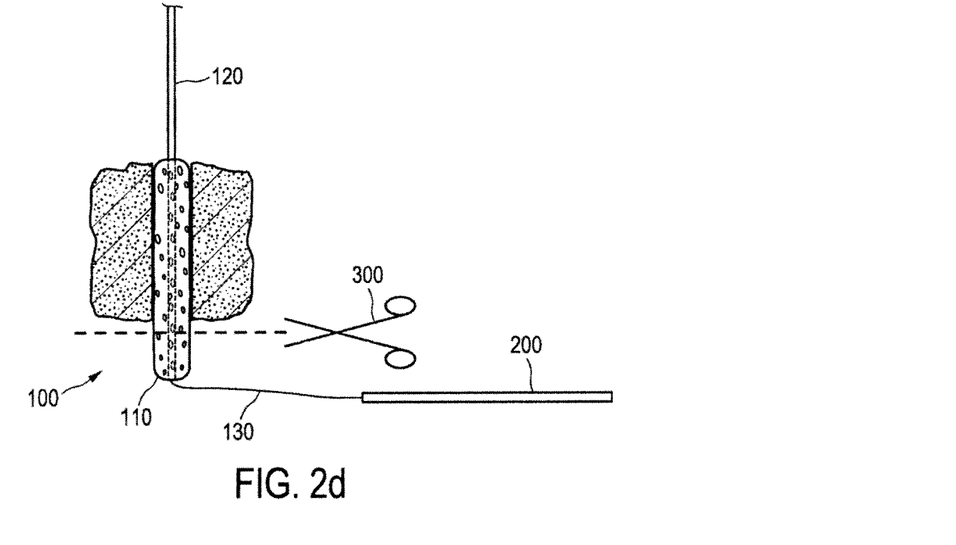

After placement, the medical device 100 can be trimmed, by way of example, by means of a scissors 300, as shown in FIG. 2d.

After placing and optionally trimming of the medical device 100, the rectal opening 14 and the skin opening 12 are sealed. For example, the rectal opening 14 can be sealed by means of suturing or stapling, while the skin opening 12 can be sealed by means of a patch.

After sealing of the fistula's ends, the fluid communication element 120 is connected to a negative pressure or vacuum source, in particular to a negative pressure or vacuum pump.

EXAMPLES

1. Concept of Manufacturing

Blocks of polyurethane foam were manufactured by an external supplier with dimensions of 100×450×735 mm. Three types of foams (orange, black and silver foams) of the same material were received. The characteristics of the foam types are detailed in table 1:

TABLE 1

|  | orange | black | silver |
| --- | --- | --- | --- |
| Foam density | $23 \pm 2.5$ kg/m$^3$ | $23 \pm 2.5$ kg/m$^3$ | $28 \pm 3.0$ kg/m$^3$ |
| Compression load | $3.9 \pm 0.8$ kPa | $3.6 \pm 1.0$ kPa | $2.95 \pm 0.85$ kPa |
| Tensile strength | min. 60 kPa | min. 60 kPa | min. 75 kPa |
| Elongation at break | min. 100% | min. 100% | min. 95% |

Cylindrical foams were mechanically cut from the blocks by means of cutting dyes. To do so, two types of dyes were used: a dye having a diameter of 12 mm for the external diameter of the polyurethane foam and a dye having a diameter of 2 mm for the inner hollow diameter of the polyurethane foam. The length of the cylinder was the 100 mm depth of the foam block. As an alternative, the foam cutting may be accomplished by means of a hydraulic press.

For the fluid communication element, a CH05 redon tube was cut from an original length of 500 mm to 440 mm (reducing the length of perforations from 150 mm to 90 mm). This component was cut in order to adapt it to the cylindrical foam of 100 mm. Additionally, the redon tube was marked to position the fixation points with the sutures.

The already cut redon drain was then introduced through the inner canal of the cylindrical foam. Both components were fixed using a braided non-absorbable polyester suture (USP 0). This suture passed through the sponge and orifice of 1 mm of the redon drain avoiding to pierce the tube with the suture needle. An overhand knot was performed and two square knots were performed on the opposed sides. The remaining ends of the suture were cut with scissors. This procedure was repeated a total of 4 times along the cylindrical foam, following the marks on the redon drain.

The fifth fixation point at the distal part of the device differed from the ones described above. Unlike the other fixation points, once the square knots were performed, one of the suture ends was not cut. This uncut end was used to create the pulling loop with a total length of 200 mm and a loop of 35 mm. This loop was performed using a double overhand knot, the remaining suture was cut with scissors.

Further, a standard male luer-lock connector was assembled to the remaining distal end of the redon drain by mechanical interference with a CH05 to CH06 adapter.

2. Usability of the Concept

A laboratory model of a complex fistula canal was manufactured by using transparent polyurethane rubber molding. The material was soft (Shore A 20) in order to stimulate its in vivo performance. This model contained a curved canal of 80 mm in length and a diameter of 8 mm.

At first, a multifilament suture was introduced through the fistula canal as seton. This corresponds to the treatment of fistulas, where the first procedure is to maintain the fistula canal open for cleansing.

Afterwards, a medical device according to the present invention was knotted from the pulling loop to the already introduced seton. In order to facilitate the introduction of the medical device, the cylindrical foam was impregnated with an Askina® hydrogel. The seton and pulling knot acted as a guide to position the cylindrical foam through the fistula canal. Once the foam covered all the fistula canal, the distal part with the pulling element was removed taking into account that no foam remained outside of the defect.

In order to apply a vacuum pressure on the canal, it was required to close both openings of the defect. The proposed method of closure by the surgeons is to use a suture in both openings. The laboratory model cannot be sutured, as it would tear the material, therefore instead of sutures it was used polyurethane adhesive pads already used on vacuum therapy for open approaches.

The standard male luer-lock connector was connected to an extension tube, already used for wound drainage. Subsequently, the extension tube was connected to a digital vacuum pump with a set point of 175 mmHg of pressure (absolute). The pump was started and the fistula canal was reduced due to the actuation of the vacuum through the whole defect.

The invention claimed is:

1. A device for treating a fistula comprising:
a) a fluid collection element comprising an open cell or porous structure, the fluid collection element comprising a proximal fluid collection portion and a distal fluid collection portion,
b) a fluid communication element comprising a tubular body extending through the proximal fluid collection portion of the fluid collection element, the tubular body comprising a proximal tube section and a distal tube section, and
c) a pulling element comprising a proximal section and a distal section,
the proximal section of the pulling element being attached to or around the distal tube section of the fluid communication element,
the distal section of the pulling element comprising a distal end extending away from the distal tube section of the fluid communication element and configured to be pulled by a grasping instrument to place the device inside a fistula,
an entirety of the pulling element being located outside of the proximal tube section of the fluid communication element,
the device further comprising:
a first attachment element secured around the proximal fluid collection portion to axially fix the proximal fluid collection portion to the fluid communication element, and
a second attachment element secured around the distal fluid collection portion to axially fix the distal fluid collection portion to the fluid communication element, so that the fluid collection element is axially fixed relative to the fluid communication element.

2. The medical device according to claim 1, wherein the pulling element comprises a loop portion.

3. The medical device according to claim 1, wherein the pulling element comprises a non-looped portion.

4. The medical device according to claim 3, wherein the pulling element is attached to the fluid collection element via the non-looped portion.

5. The medical device according to claim 1, wherein the pulling element engages at least one hole and/or at least one perforation that is arranged on the distal tube section of the fluid communication element.

6. The medical device according to claim 1, wherein the pulling element is attached to or around the distal tube section of the fluid communication element by a knot, thread, clip and/or material bonding engagement.

7. The medical device according to claim 1, wherein the pulling element is attached to the distal fluid collection portion of the fluid collection element by knotting.

8. The medical device according to claim 1, wherein the pulling element is a thread.

9. The medical device according to claim 1, wherein the distal tube section of the fluid communication element is surrounded by the fluid collection element.

10. The medical device according to claim 1, wherein the distal tube section of the fluid communication element comprises holes and/or perforations.

11. The medical device according to claim 10, wherein the holes and/or perforations in the distal tube section of the fluid communication element extend along an entire length of the fluid collection element.

12. The medical device according to claim 1, wherein the fluid communication element comprises a connector.

13. A medical kit comprising a medical device according to claim 1 and at least one component selected from a group consisting of negative pressure or vacuum source, extension tube, fluid collection vessel, sterile filter, grasping instrument, lubricant, syringe, suture, sealing patch, scissors and stapler.

14. The medical device according to claim 1, further comprising a plurality of attachment elements secured around the fluid collection element at a plurality of fixation sites along a length of the fluid collection element between the first attachment element and the second attachment element to axially fix the fluid collection element to the fluid communication element.

15. The medical device according to claim 14, wherein the plurality of attachment elements constrict the fluid collection element at the plurality of fixation sites.

16. The medical device according to claim 1, wherein the entirety of the pulling element is located outside of the proximal tube section and distal tube section of the fluid communication element.

* * * * *